United States Patent [19]
Thomasson

[11] Patent Number: 5,557,681
[45] Date of Patent: Sep. 17, 1996

[54] ELECTRONIC STETHOSCOPE

[76] Inventor: Samuel L. Thomasson, 1038 E. Hearn Way, Gilbert, Ariz. 85234

[21] Appl. No.: 125,236

[22] Filed: Sep. 24, 1993

[51] Int. Cl.$^6$ ........................................................... A61B 7/04
[52] U.S. Cl. ............................................... 381/67; 327/553
[58] Field of Search ............................ 381/67, 120, 109, 381/187; D24/134; 328/167; 307/520, 521

[56] References Cited

U.S. PATENT DOCUMENTS

| | | | |
|---|---|---|---|
| 3,160,708 | 12/1964 | Andries et al. | 381/187 |
| 3,171,406 | 3/1965 | Baum et al. . | |
| 3,182,129 | 5/1965 | Clark et al. | 381/109 |
| 3,539,724 | 4/1966 | Cefaly et al. | 381/109 |
| 4,220,160 | 9/1980 | Kimball et al. | 381/67 |
| 4,226,248 | 10/1980 | Manoli . | |
| 4,498,188 | 2/1985 | Hofer | 381/67 |
| 4,598,417 | 7/1986 | Deno | 381/67 |
| 4,619,268 | 10/1986 | Uphold et al. . | |
| 4,628,939 | 12/1986 | Little et al. . | |
| 4,783,813 | 11/1988 | Kempka | 381/67 |
| 4,783,814 | 11/1988 | Foley . | |
| 4,792,145 | 12/1988 | Eisenberg et al. | 381/67 |
| 4,878,501 | 11/1989 | Shue . | |
| 5,010,890 | 4/1991 | Pfohl et al. . | |

OTHER PUBLICATIONS

Don Lancaster, *Active Filter Cookbook*, 1975, p. 162.

*Primary Examiner*—Curtis Kuntz
*Assistant Examiner*—Ping W. Lee
*Attorney, Agent, or Firm*—Cahill, Sutton & Thomas P.L.C.

[57] ABSTRACT

An electronic stethoscope includes a microphone mounted in a resilient collar in a hand-held case. The microphone is coupled to an active filter having independently and continuously adjustable bandwidth and center frequency. A switch bypasses the active filter when the user wishes to hear all of the sounds detected by the microphone. The controls for bandwidth and center frequency are located on one side of the case and can be manipulated by the hand holding the stethoscope. The volume or gain of the stethoscope is adjusted by a third control located on the one side of the stethoscope. The controls can be linear or rotary or combinations thereof. The output signal from the active filter passes through a filter having a frequency response inverse to that of the human ear, is amplified, and is coupled to headphones which plug into a socket on the rear of the case. The active filter is either a state variable filter or a Butterworth filter, has a maximum bandwidth of at least ten octaves, and is stable at all settings of the controls.

17 Claims, 5 Drawing Sheets

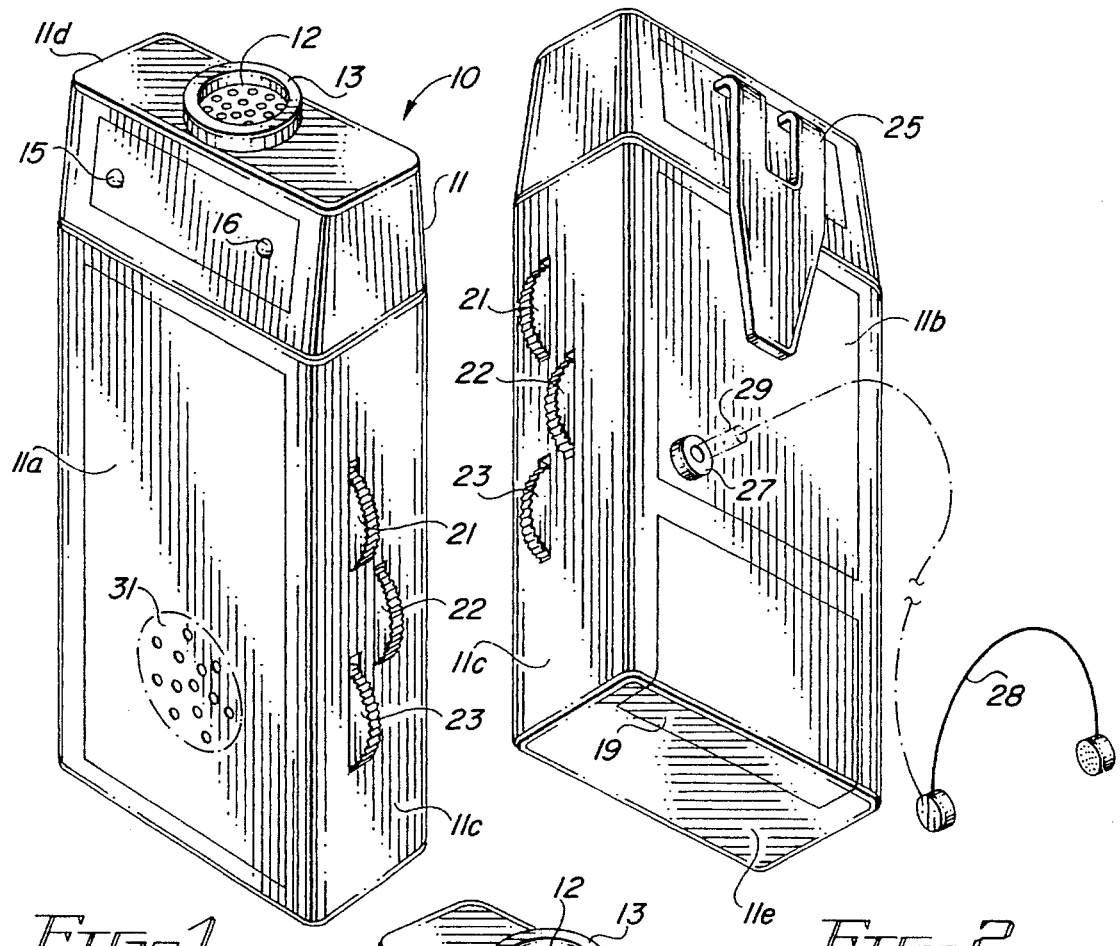
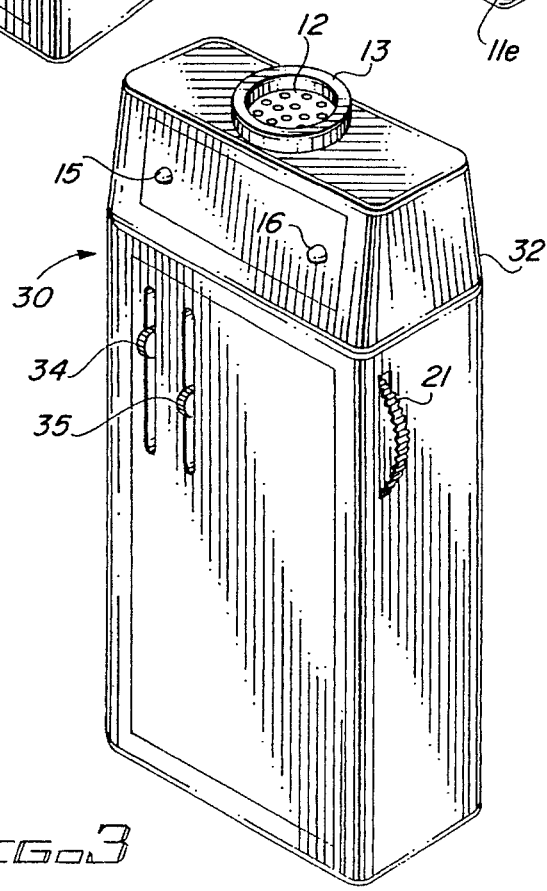

ELECTRONIC STETHOSCOPE

BACKGROUND OF THE INVENTION

The invention relates to electronic stethoscopes and, in particular, to a hand-held electronic stethoscope having an active filter in which the center frequency and bandwidth are continuously adjustable over the entire range of somatic sounds.

Originally developed in 1816 by the French physician René Laënnec to permit auscultation without actually touching an ear to the patient, a traditional or acoustic stethoscope gathers sound in a chest piece and conveys the sound to a physician's ears through a tube attached to the chest piece. On one side of the chest piece is a bell-shaped metal cup rimmed with rubber for transmitting sounds of lower pitch and on the other side of the chest piece is a wider, flatter cup covered with a thin, taut, plastic diaphragm for transmitting sounds of higher pitch. A tube connects the chest piece to a Y fitting for splitting the sound between two tubes having earpieces at the free ends thereof.

An acoustic stethoscope limits the mobility of a physician. The tube from the chest piece to the ear piece must be relatively short to minimize attenuation of the sound. Lack of mobility can be a critical problem, e.g. for an anesthesiologist who must either be tethered to a patient or leave the patient unmonitored while attending to other duties within an operating room. Clinical physicians often find it necessary to be away from a patient and yet still wish to monitor the patient.

An acoustic stethoscope can not adjust the loudness of the sounds and can not separate sounds of interest from other sounds, although some manufacturers adjust the thickness of the diaphragm and the shape of the bell to emphasize sounds in a particular frequency range. It was not realized at the time that Dr. Laënnec had an acute sense of hearing and was able to distinguish sounds readily. Other physicians, without his aural acuity, have a more difficult time using a stethoscope to its full potential.

Electronic stethoscopes can overcome these difficulties and provide other advantages, such as powering a loudspeaker for several people to hear the sound simultaneously. An electronic stethoscope includes a microphone for converting sound waves into an electrical signal, an amplifier, and a filter to remove extraneous noises, particularly higher frequencies, from the electrical signal. The amplified, filtered signal is then coupled to small speakers in a headphone worn by the physician or is amplified further and coupled to a loudspeaker.

The filter in an electronic stethoscope has been the subject of many and varied proposals in the prior art. Some patents disclose modifying the frequency response of the filter by switching capacitors into or out of the filter, e.g. U.S. Pat. Nos. 4,534,058 (Hower); 4,528,690 (Sedgwick); and 4,254,302 (Walsh). Other patents, such as U.S. Pat. No. 4,226,248 (Manoli), disclose selecting one or more bandpass filters by means of a switch.

In all such filters, the frequency response of the filter is changed in discrete steps rather than continuously. Electronic stethoscopes tend to be application specific because the filters can not be adjusted continuously over the entire band of somatic sounds, approximately 1–3,000 hz. This range, more than ten octaves, is difficult to cover in a continuously adjustable active filter without instability, i.e. without oscillation.

While providing some enhancement of a sound of interest, the patented systems are not as flexible or as easy to use as many physicians desire. The patents listed above describe apparatus which cannot be held in one hand or fit into a pocket and the controls for which are not easily manipulated by one hand. In addition, simple filtration is often unsuited to selecting the sound of interest to a physician. For example, tailoring the frequency response of a stethoscope to heart sounds, or a particular heart sound, often means that the stethoscope is unsuited to monitoring other sounds, e.g. respiration.

Many sounds of interest are near the threshold of human hearing, i.e. below thirty hz. Bandpass filters or high pass filters may attenuate low frequency sounds below the threshold of hearing. Often, a physician wants a sound emphasized without eliminating all other sounds since the other sounds provide a frame of reference. Occasionally, a physician wants to hear sounds unfiltered, i.e. a faithful reproduction of all sounds detected by the microphone. The prior art does not address these considerations.

In view of the foregoing, it is therefore an object of the invention to provide an electronic stethoscope which improves a physician's ability to detect, isolate, amplify, and listen to the sounds produced within a patient.

Another object of the invention is to provide a portable, hand-held electronic stethoscope that can be operated by the hand supporting it.

A further object of the invention is to provide an electronic stethoscope which can transmit somatic sounds to a physician's headset or to a remote speaker.

Another object of the invention is to provide an electronic stethoscope having an improved filter in which the bandwidth and center frequency of the filter can be adjusted independently throughout the entire range of somatic sounds.

A further object of the invention is to provide an adjustable, stable, wide band, state variable filter.

Another object of the invention is to provide an adjustable, stable, wide band, Butterworth filter.

A further object of the invention is to provide an electronic stethoscope which can reproduce somatic sounds with high fidelity, by-passing the active filter.

Another object of the invention is to provide an electronic stethoscope in which the output signal is corrected for the frequency response of the human ear.

SUMMARY OF THE INVENTION

The foregoing objects are achieved in the invention in which an electronic stethoscope includes a microphone mounted in a resilient collar in a hand-held case. The microphone is coupled to an active filter having independently and continuously adjustable bandwidth and center frequency. A switch bypasses the active filter when the user wishes to hear all of the sounds detected by the microphone. The controls for bandwidth and center frequency are conveniently located on one side of the case and can be manipulated by the hand holding the stethoscope. The volume or gain of the stethoscope is adjusted by a third control located on one side of the stethoscope. The controls can be linear or rotary or combinations thereof. The output signal from the active filter passes through a filter having a frequency response inverse to that of the human ear, is amplified, and is coupled to headphones which plug into a socket in the rear of the case. In one embodiment of the invention, the active filter is a state variable filter. In another embodiment of the invention, the active filter is a Butterworth filter. In both embodiments, the active filter has a maximum bandwidth of at least ten octaves and is stable at all settings of the controls.

BRIEF DESCRIPTION OF THE DRAWINGS

A more complete understanding of the invention can be obtained by considering the following detailed description in conjunction with the accompanying drawings, in which:

FIG. 1 is a front perspective view of an electronic stethoscope constructed in accordance with the invention;

FIG. 2 is a rear perspective view of the stethoscope shown in FIG. 1;

FIG. 3 is a front perspective view of an electronic stethoscope constructed in accordance with an alternative embodiment of the invention;

DETAILED DESCRIPTION OF THE INVENTION

Figure 4:
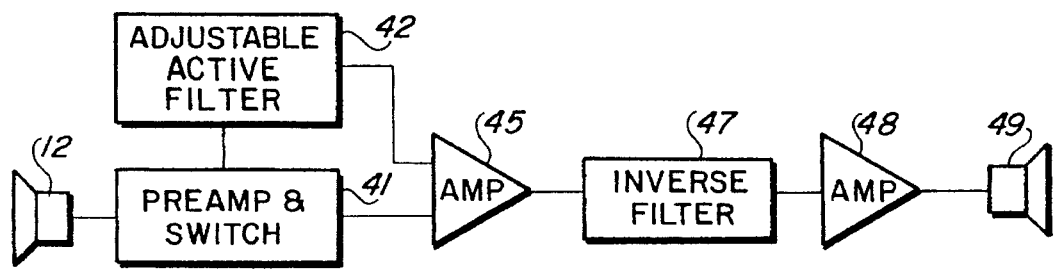
FIG. 4 is a block diagram of an electronic stethoscope constructed in accordance with the invention.

FIGS. 1 and 2 are perspective views of a first embodiment of an electronic stethoscope constructed in accordance with the invention. In FIGS. 1 and 2, stethoscope 10 includes case 11 for containing the electronics and controls. Case 10 can have any suitable shape conveniently fitting within the hand. As illustrated in FIGS. 1 and 2, case 11 has broad, rectangular front and back sides 11a and 11b, interconnected by first and second narrow sides, of which side 11c is visible in FIGS. 1 and 2. Top 11d and bottom 11e complete the enclosure.

Microphone 12 is connected to top 11e by resilient collar 13. Collar 13 prevents vibration caused by handling case 11 from being coupled to microphone 12. Since microphone 12 is slightly recessed in collar 13, the collar serves a second purpose in acting as an acoustic seal around the microphone when touched against a patient. Light emitting diodes (LEDs) 15 and 16 are located in front side 11a and indicate the operation of the stethoscope. LED 15 is luminous when power is on and LED 16 is luminous when the stethoscope is being operated in a scan mode, described herein. The LEDs preferably emit different colors, such as red or green.

Side 11c includes rotary controls 21, 22, and 23. Control 21 adjusts volume and turns the stethoscope on or off. Control 22 adjusts center frequency and includes a switch for bypassing the active filter. Control 23 varies the bandwidth. These three functions are described in more detail in conjunction with FIGS. 5 and 10. On back side 11b (FIG. 2), belt clip 25 provides a means for attaching electronic stethoscope 10 to a belt or other support. Also located on the rear of stethoscope 10 is socket 27 for connecting headphones 8 to the stethoscope by way of plug 29.

Front side 11a includes optional speaker 31 for projecting the somatic sounds detected by microphone 12. Speaker 31 is bypassed when plug 29 is inserted into socket 27. Headphones 28 provide a means for listening to somatic sounds privately while speaker 31 provides a means for several people to listen to somatic sounds simultaneously. Other means can be used for making the sounds audible to one or more people, including the patient. For example, an infrared transmitter (not shown) on case 11 can be used to couple the stethoscope to a remote receiver and amplifier for reproducing the sounds over a loudspeaker or headphones. Battery cover 19 provides access to one or more batteries stored within case 11.

FIG. 3 illustrates an electronic stethoscope constructed in accordance with an alternative embodiment of the invention in which linear controls are used instead of two of the rotary controls. An advantage of linear controls is that the setting of a linear control is more easily discerned than the setting of a rotary control. The circuitry within stethoscope 30 is identical to the circuitry within stethoscope 10. In stethoscope 30, potentiometer 34 extends through a first slot in case 32 and controls center frequency. Potentiometer 35 extends through a second slot, parallel to the first slot, in case 32 and controls bandwidth. Rotary volume control 21 is located on side 38 of stethoscope 30, thereby distinguishing the volume control from the controls for the filter. Elements in FIG. 3 common to FIG. 1 have the same reference number as in FIG. 1.

As known in the art, potentiometers include resistive material connected between two terminals and a wiper in sliding electrical contact with the resistive material and connected to a third terminal. A potentiometer can have a linear, audio, or exponential "taper." A linear taper means that resistance changes in proportion to the movement of the wiper. Potentiometers used in implementing the invention preferably have an audio taper, although any taper can be used. As used herein, "linear" refers to the motion of the wiper, not the taper.

FIG. 4 is a block diagram showing the major components of an electronic stethoscope constructed in accordance with the invention. Preamplifier 41 amplifies the signal from microphone 12 and couples the amplified signal either to adjustable active filter 42 or to amplifier 45 under the control of a switch within the preamplifier. In a preferred embodiment of the invention, the switch is mechanically connected to control 22 (FIG. 1), like the on-off switch on the volume control of a small radio. When control 22 is in the "off" position, filter 42 is bypassed. Filter 42 has a variable center frequency and an independently adjustable bandwidth operating continuously over the entire range of somatic sounds, e.g. 1–3000 hz.

Amplifier 45 provides isolation between filter 42 and filter 47 and has a small gain. Inverse filter 47 has a transfer characteristic that is the inverse of the frequency response of the human ear, i.e. sounds below 50 hz. are amplified more than sounds having a frequency higher than 50 hz. The output signal from inverse filter 47 is amplified by amplifier 48 and coupled to speaker 49. Speaker 49 can be a speaker within the case of the stethoscope or the speakers in a headphone.

Figure 5:
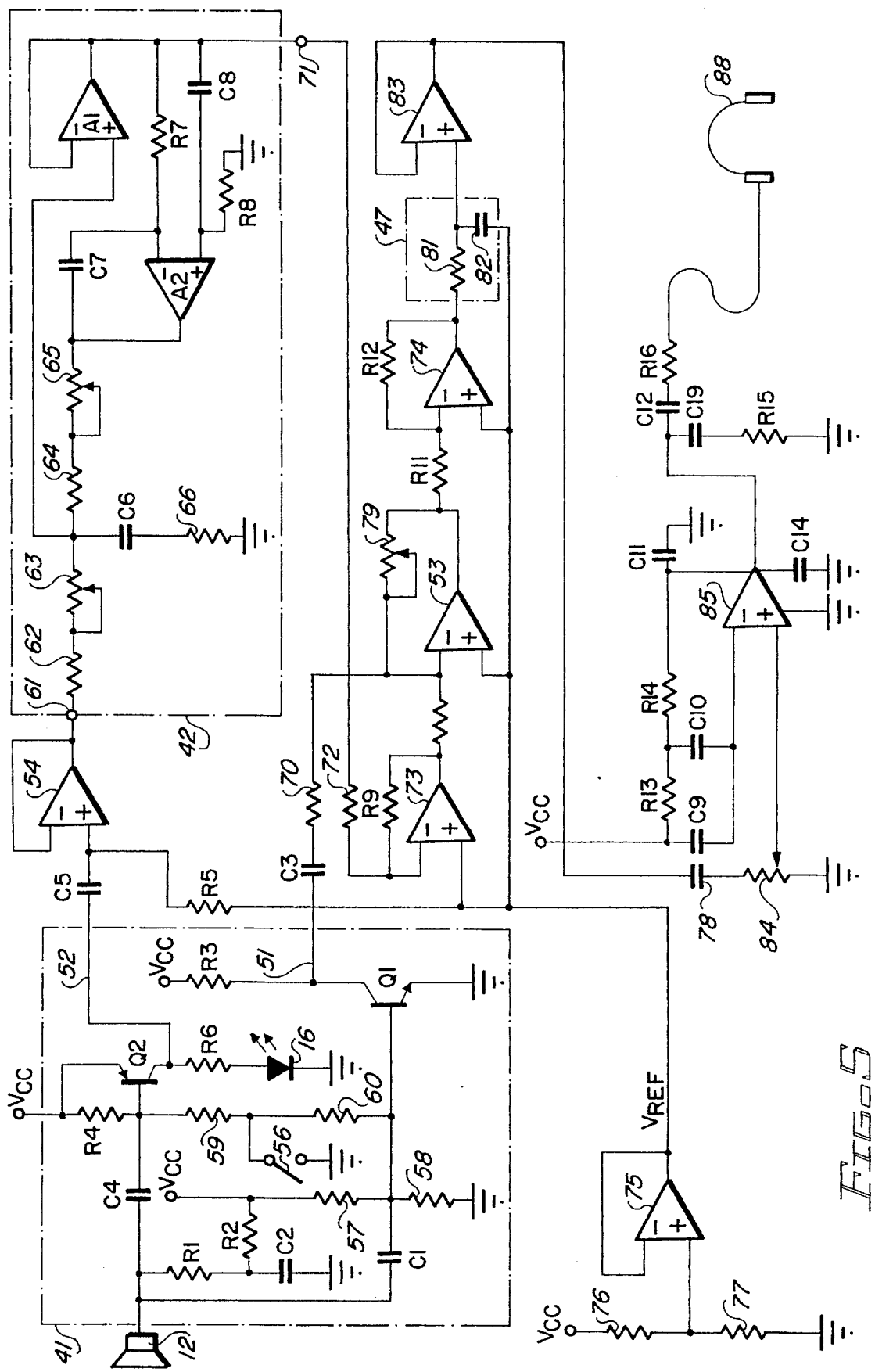
FIG. 5 is a circuit diagram of an electronic stethoscope constructed in accordance with the invention.

FIG. 5 is a schematic of an electronic stethoscope constructed in accordance with the invention. In FIG. 5, the signal from microphone 12 is amplified in preamplifier 41 by transistors $Q_1$ and $Q_2$. Output 51 of preamplifier 41 is coupled to amplifier 53 and output 52 of preamplifier 41 is coupled to amplifier 54. Switch 56 determines which of transistors $Q_1$ and $Q_2$ is biased off. Specifically, when switch 56 is open, the base-emitter junction of transistor $Q_2$ is reverse biased, turning it off. The signal from microphone 12 is amplified by transistor $Q_1$ and is coupled through resistor 70 to the input of amplifier 53.

The bias on the base of transistor Q1 is determined by a voltage divider including resistors 57 and 58. When switch 56 is closed, resistor 60 is connected in parallel with resistor 58, reducing the voltage on the base and reverse biasing the base-emitter junction of transistor $Q_1$. At the same time, one end of resistor 59 is grounded and the base-emitter junction of transistor $Q_2$ is forward biased. The signal from microphone 12 is amplified by transistor $Q_2$ and is coupled by amplifier 54 to active filter 42.

The collector current through transistor Q2 passes through LED 16, causing the LED to emit light. This visual signal reminds the user that the active filter is in use. The brightness of LED 16 is affected by the amplitude of the signal from microphone 12, e.g. one can determine pulse rate from the LED.

Active filter 42 is a type of Butterworth filter and is similar to the filter disclosed in U.S. Pat. No. 4,226,248 (Manoli). The Manoli patent discloses a filter having a center frequency variable between 150 and 1000 hz, i.e. the upper frequency limit of the filter is 2000 hz. While disclosed in the Manoli patent as suitable for electrocardiograph (ECG) purposes, this frequency limit is inadequate for somatic sounds. Filter 42 in FIG. 5 has a center frequency that can be varied between 1 and 1500 hz, and a bandwidth that can be varied from 1–3000 hz. The filter disclosed in the Manoli patent does not include resistor 66, which keeps the gain of filter 42 below unity (zero db).

Figure 6:
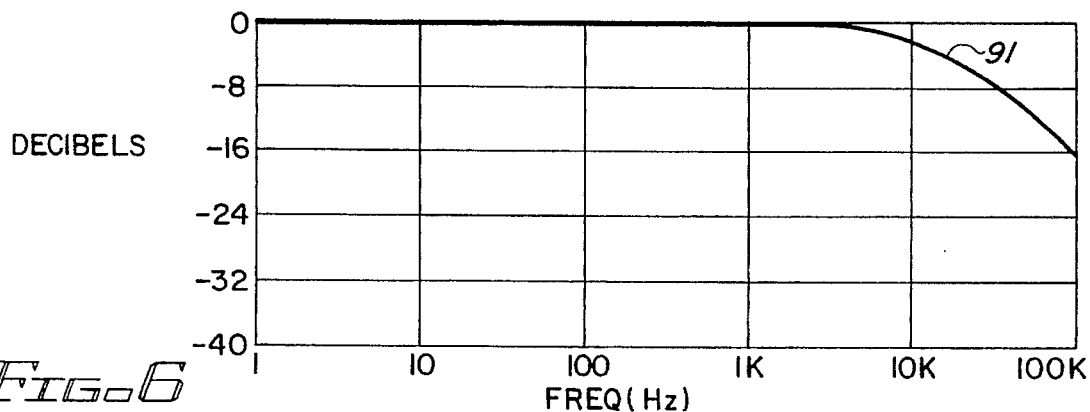
FIG. 6 is a waveform illustrating the frequency response of the filter shown in FIG. 5 at a particular setting of the controls.
Figure 7:
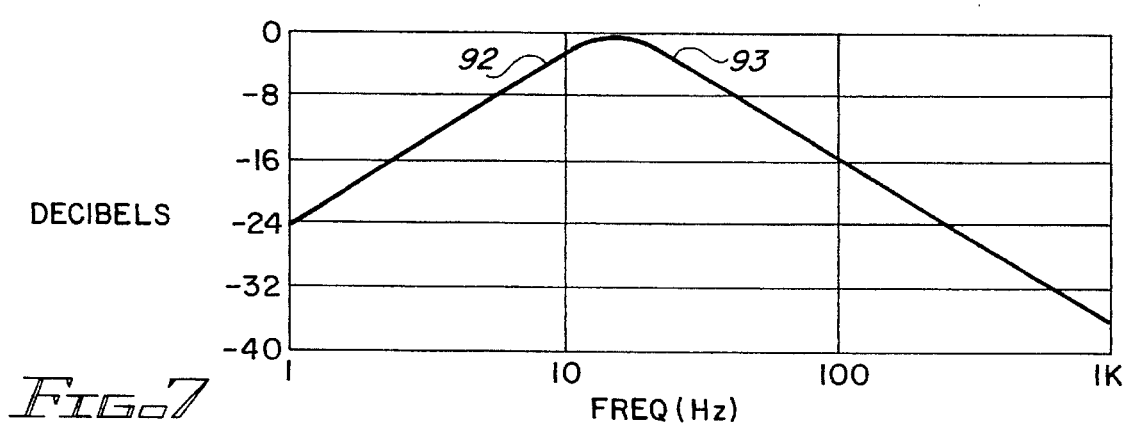
FIG. 7 is a waveform illustrating the frequency response of the filter shown in FIG. 5 at another setting of the controls.
Figure 8:
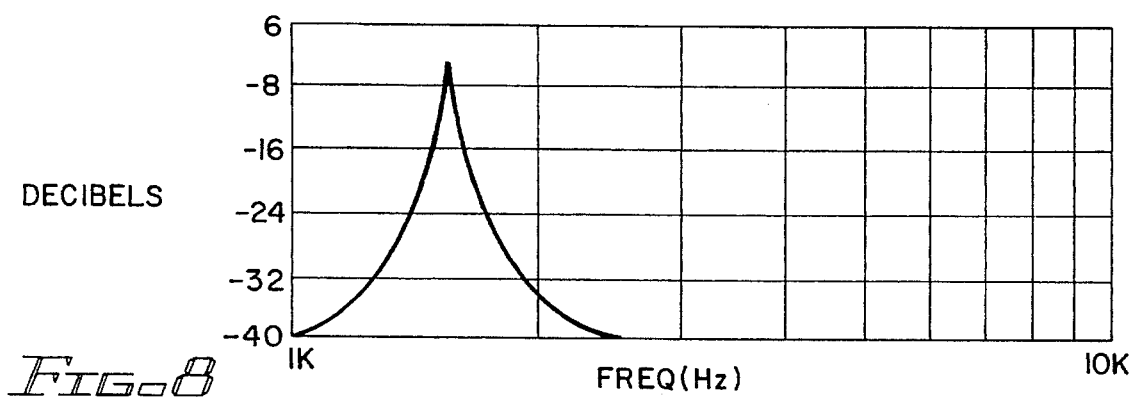
FIG. 8 is a waveform illustrating the frequency response of the filter shown in FIG. 5 at a third setting of the controls.

The operation of filter 42 is illustrated in FIGS. 6–8. Potentiometer 63 controls the bandwidth of filter 42 and potentiometer 65 controls the center frequency. Resistors 62 and 64 provide a minimum resistance when potentiometers 63 and 64 are set to minimum resistance (zero ohms).

FIG. 6 illustrates the frequency response of filter 42 when potentiometer 63 is at its minimum resistance and potentiometer 65 is at its maximum resistance. As can be seen from FIG. 6, the frequency response filter 42 is essentially flat through 3 kilohertz, dropping to −3 db at approximately 13,000 hz as indicated by reference number 91.

FIG. 7 illustrates the frequency response of filter 42 when potentiometer 63 is at its maximum resistance and potentiometer 65 is at its maximum resistance. In this case, the filter has a center frequency of approximately 15 hz and a bandwidth of approximately 15 hz. As used herein bandwidth refers the difference in frequency between −3 db points on the response curve. That is, in FIG. 7, the response curve crosses −3 db at approximately 10 hz, as indicated by reference number 92, and crosses −3 db again at approximately 25 hz, as indicated by reference number 93, for a bandwidth of 15 hz.

FIG. 8 illustrates response of filter 42 when potentiometer 63 is at maximum resistance and potentiometer 65 is at minimum resistance. The center frequency is approximately 1500 hz and the bandwidth is approximately 100 hz. The peak of the frequency response curve is one or two db below zero db and the filter is stable.

Figure 9:
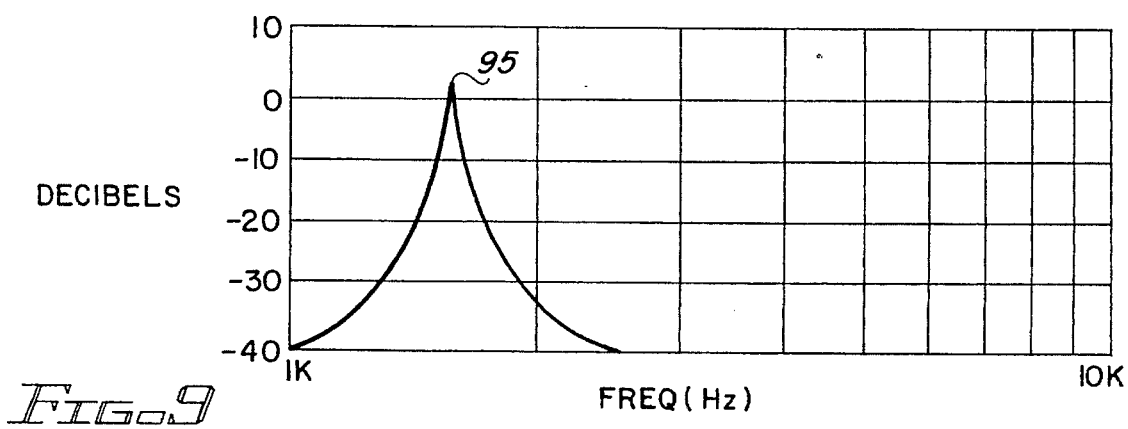
FIG. 9 is a waveform illustrating the frequency response of an unstable active filter.

FIG. 9 illustrates the response curve of a filter constructed in accordance with FIG. 4 of the Manoli Patent using the same components and settings as filter 42. At center frequency 95, the gain of the filter is greater than unity (zero db). Because the filter has a gain greater than one, the filter is unstable and oscillates. In addition, the filter in the Manoli patent is not described as adjustable. One component is illustrated as adjustable but this has been found to vary center frequency and amplitude, which is undesirable. Thus, the filter described by Manoli is unsuited to an electronic stethoscope including a single, wide band filter having continuously variable bandwidth and center frequency.

In FIG. 5, output terminal 71 of filter 42 is coupled to the inverting (−) input of amplifier 73 by resistor 72. Amplifiers 73, 54 and 74 form a cascaded amplifier section having wide bandwidth and DC coupling. The amplifiers saturate when an excessively loud sound is received at microphone 12 and the large DC voltage from the saturating amplifiers is blocked by coupling capacitor 78. The saturating amplifiers act like a squelch circuit to prevent an excessively loud sound from being produced by headphones 88.

Because of the DC coupling, cascaded amplifiers 73, 54 and 74 are not referenced to ground but instead have their non-inverting (+) inputs coupled to a source of reference voltage, amplifier 75. Amplifier 75 has its non-inverting input connected to the junction of resistors 76 and 77. Resistors 76 and 77 are a voltage divider connected between the supply voltage ($V_{cc}$) and electrical ground. The output of amplifier 75 is a stable reference voltage $V_{ref}$ between ground and the supply voltage and enables amplifiers 73, 54, and 74 to handle alternating current, i.e. a signal alternating about reference voltage $V_{ref}$ as an AC ground.

The output from amplifier 74 is coupled to inverse filter 47, shown in FIG. 5 as a low pass, single stage, RC filter. In a preferred embodiment of the invention, inverse filter 47 includes resistor 81 and capacitor 82 and has a time constant of 0.01 seconds.

The output from inverse filter 47 is coupled through isolation amplifier 83 to potentiometer 84 and power amplifier 85. The output of power amplifier 85 is coupled to headphones 88. Potentiometer 84 is not a volume control but is an internal adjustment for controlling the maximum gain of the stethoscope. The volume control for the stethoscope is potentiometer 79 connected in the feedback path of amplifier 54. The resistors and capacitors connected between the inverting input of amplifier 85 and the supply voltage are a low pass filter for preventing feedback through the power supply to other amplifiers.

Figure 10:
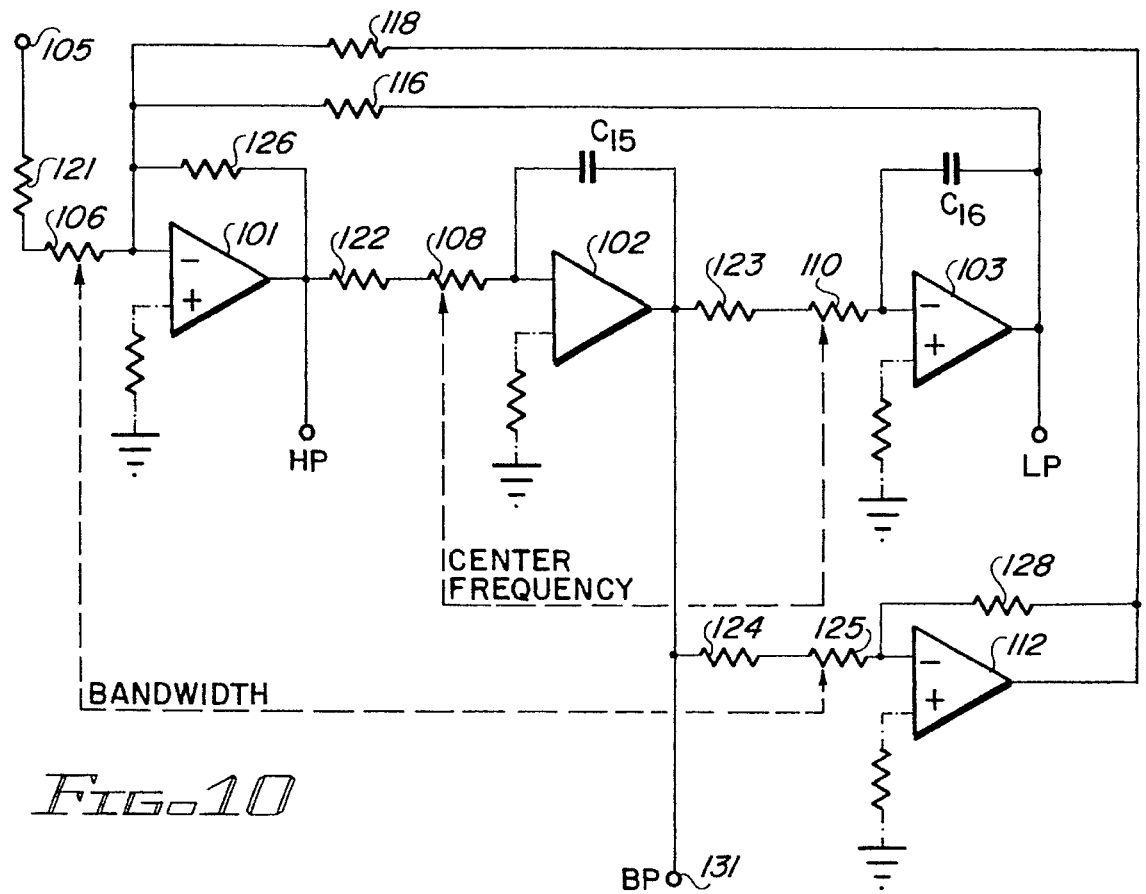
FIG. 10 is a circuit diagram of a state variable filter constructed in accordance with the invention.

FIG. 10 illustrates an alternative embodiment of active filter 42. Filter 100 is a state variable filter including three cascaded, resistively coupled amplifiers 101, 102, and 103. Input terminal 105 is coupled to the inverting input of amplifier 101 by potentiometer 106. The output of amplifier 101 is coupled to the inverting input of amplifier 102 by potentiometer 108. The output of amplifier 102 is coupled to the inverting input of amplifier 103 by potentiometer 110 and to the inverting input of amplifier 112 by potentiometer 125.

Potentiometers 108 and 110 are ganged (mechanically connected) to control the center frequency of filter 100. Potentiometers 106 and 125 are ganged and control the bandwidth of filter 100. The output of amplifier 103 is coupled to the inverting input of amplifier 101 by resistor 116. The output of amplifier 112 is coupled to the inverting input of amplifier 101 by resistor 118. Resistors 121, 122, 123, and 124 provide a minimum resistance when the potentiometer in series therewith is set to zero resistance.

State variable filters are known in the art, for example U.S. Pat. No. 4,628,939 (Little et al.) discloses a state variable filter in FIG. 5 thereof. The state variable filter disclosed in Little et al. has a step-wise variable center frequency which is changed by switching resistors of different values in parallel with the interstage resistors between the cascaded amplifiers. The filter described by Little et al. has an overall bandwidth of 10–1000 hz which can be narrowed to either 10–100 hz or 100–1000 hz by selection of the appropriate resistances.

The invention achieves a continuous, independent adjustment of center frequency and bandwidth over a considerably wider range than the circuit disclosed in the Little et al. patent by implementing the adjustable filter in a manner contrary to accepted design principles for state variable filters. For example, it is accepted that feedback resistors 116, 118, and 126, should be in the ratio of 1:1:1. On the contrary, in filter 100, feedback resistors 116, 118, and 126 are in a ratio of 100:10:1. Similarly, the resistance of resistor 128 is equal to the resistance of resistor 118 (ratio of 1:1) rather than a predetermined fraction of resistor 125. It has been found that these two relationships permit one to attain wide bandwidth and stability. Also, by keeping resistors 118 and 128 equal, one can apply a higher amplitude input signal to filter 100 without saturating the amplifiers than one can apply to state variable filters of the prior art.

Output 131 is the bandpass output terminal for filter 100. State variable filters have the advantage of also being usable both as low pass filters and high pass filters. The output of amplifier 101 is the high pass output terminal and the output of amplifier 103 is the low pass output terminal. Thus, while a state variable filter does not have as flat a frequency response as a Butterworth filter and has more components, the state variable filter has the advantage of providing three outputs: low pass, bandpass, and high pass. In a preferred embodiment of the invention, only the bandpass output is used.

The non-inverting inputs to amplifiers 101, 102, and 103 can be coupled to an AC ground, as in filter 42, or coupled to ground through a resistor, as shown in dotted line in FIG. 10. Either connection can be used with active filters 42 and 100.

Figure 11:
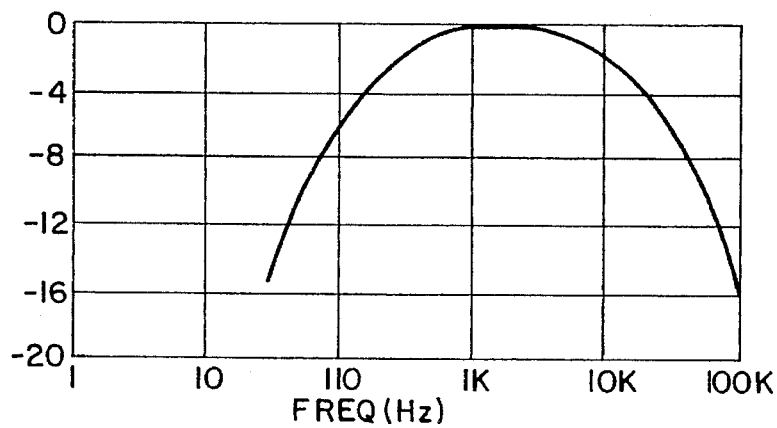
FIG. 11 is a waveform illustrating the frequency response of the circuit shown in FIG. 10 at a particular setting of the controls.

FIGS. 11, 12, 13, and 14 illustrate the frequency response characteristic of filter 100 at different settings of the center frequency and bandwidth potentiometers. FIG. 11 illustrates the frequency response of the filter with potentiometers 106, 108, 110, and 114 all set to their minimum resistance. At this setting, the bandwidth, measured at the −3 db points, is approximately 150–15,000 hz, with a center frequency of 1500 hz.

Figure 12:
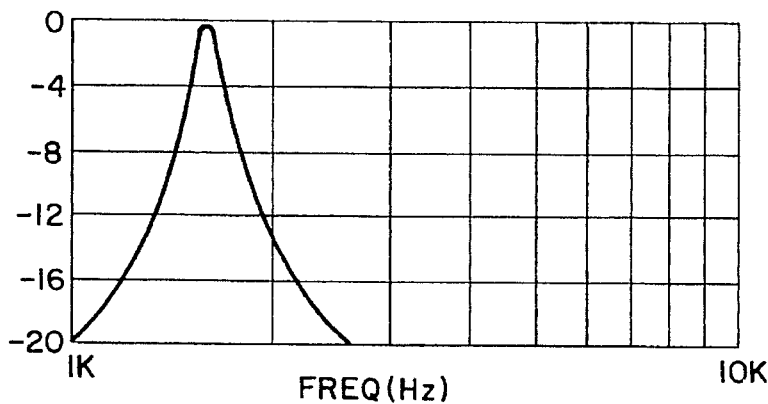
FIG. 12 is a waveform illustrating the frequency response of the circuit shown in FIG. 10 at another setting of the controls.

FIG. 12 illustrates the frequency response with potentiometers 108 and 110 set to their minimum resistances and potentiometers 106 and 114 set to their maximum resistances. At these settings, filter 100 has a center frequency of approximately 1500 hz and a bandwidth of approximately 100 hz at −3 db.

Figure 13:
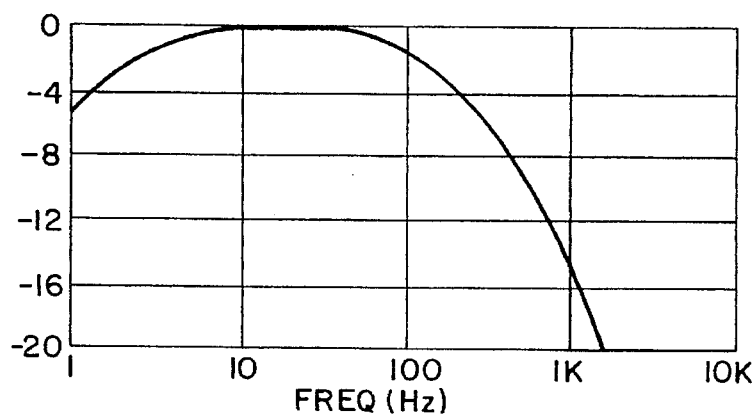
FIG. 13 is a waveform illustrating the frequency response of the circuit shown in FIG. 10 at a third setting of the controls.

FIG. 13 illustrates the frequency response of filter 100 with potentiometers 108 and 110 set to their maximum resistance and potentiometers 106 and 114 set to their minimum resistance. In this case, filter 100 has a bandwidth of approximately 150 hz and a center frequency of approximately 15 hz.

Figure 14:
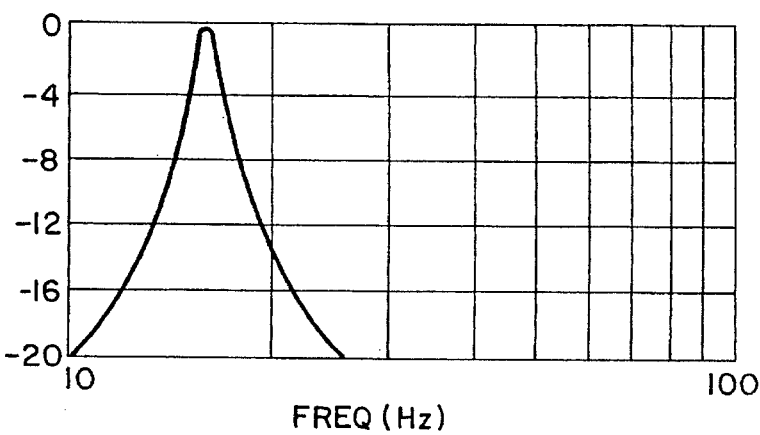
FIG. 14 is a waveform illustrating the frequency response of the circuit shown in FIG. 10 at a fourth setting of the controls.

FIG. 14 illustrates the frequency response of filter 100 with potentiometers 106, 108, 110, and 114 set to their maximum resistance. In the case, filter 100 has a center frequency of approximately 15 hz and a bandwidth of about 2 hz at −3 db.

In all of the foregoing examples, filter 100 is stable for any setting of bandwidth and center frequency, a result achieved by designing the filter in a manner contrary to the prior art.

Figure 15:
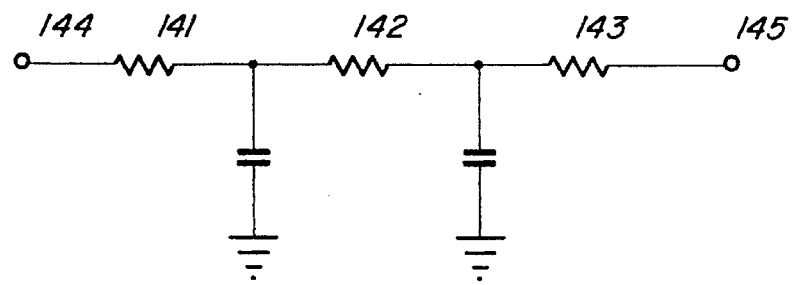
FIG. 15 is a circuit diagram of an alternative embodiment of an inverse filter for use in the circuit shown in FIG. 5.

FIG. 15 illustrates an alternative embodiment of inverse filter 47. Filter 140 is a two stage RC filter including resistors 141, 142, and 143 series connected between input terminal 144 and output terminal 145. Connected between the junctions of the resistors and ground

Having thus described the invention, it will be apparent to those of skill in the art that various modifications can be made within the scope of the invention. For example, instead of a collar, the microphone can be mounted in a resilient sheet fitting the top of the stethoscope and having a hole fitting the outside diameter of the microphone. The embodiment shown in FIG. 5 uses a single battery and an AC ground. One could substitute a pair of batteries connected in series with the junction thereof as AC ground. It is preferred to use the state variable filter simply as a bandpass filter. One could use all three outputs by adding a single pole, three position switch to select one output for connection to amplifier 45. For a handheld stethoscope, a simpler construction (without the three position switch) is preferred. Microphone 12 need not be permanently attached to case 11 but can frictionally engage collar 13. In this way, microphone 12 is removable and can be connected to case 11 by a retractable cord. Socket 27, and LEDs 15 and 16, can be located at any convenient place on case 11. Other transducers can be substituted for microphone 12 as a source of signal, e.g. ECG or EEG (electroencephalograph) probes. The invention can be used for other than medical applications, e.g. any application dealing with low frequency signals such as seismic waves or animal sounds. are capacitors are 146 and 147. The frequency response of filter 140 has a steeper roll-off at high frequencies than a single stage filter and is preferred when working in noisy environments.

The following tables list the components used in one embodiment of the invention. These components are for example only. Other components can be used depending upon the particular application and frequency.

TABLE I

| FIG. 5 | |
|---|---|
| 16 | LED |
| 57 | 1.2 MΩ |
| 58 | 100 kΩ |
| 59 | 150 kΩ |
| 60 | 68 kΩ |
| 62, 64 | 100 Ω |
| 63, 65, 79 | 100 kΩ |
| 66 | 10 Ω |
| 70, 72, 81, 84 | 10 kΩ |

TABLE I-continued

FIG. 5

| | |
|---|---|
| 73, 54, 74, 75, 83 | LM324 |
| 85 | LM386 |
| 76, 77 | 1 kΩ |
| 78, 82 | 1 μf |
| $R_1, R_2$ | 2000 Ω |
| $R_3, R_6$ | 1000 Ω |
| $R_4$ | 8200 Ω |
| $R_5, R_7, R_8, R_9, R_{10}, R_{11}$ | 10 kΩ |
| $R_{12}$ | 100 kΩ |
| $R_{13}, R_{14}$ | 200 Ω |
| $R_{15}$ | 10 Ω |
| $R_{16}$ | 200 Ω |
| $C_1, C_3, C_4, C_5$ | 1 μf |
| $C_2, C_{12}$ | 100 μf |
| $C_6, C_7, C_8, C_{11}$ | 0.1 μf |
| $C_9, C_{10}$ | 220 μf |
| $C_{13}, C_{14}$ | 0.05 μf |
| $A_1, A_2$ | LM324 |
| $Q_1$ | 2N2222 |
| $Q_2$ | 2N2907 |

TABLE II

FIG. 10

| | |
|---|---|
| 101, 102, 103, 112 | LM324 |
| 106, 108, 110, 125 | 100 kΩ |
| 121, 122, 123, 124 | 2 kΩ |
| 126 | 1 kΩ |
| 118, 128 | 10 kΩ |
| 116 | 100 kΩ |
| C15, C16 | .01 μf |

TABLE III

FIG. 15

| | |
|---|---|
| 141 | 10 kΩ |
| 142, 143 | 100 kΩ |
| 146 | 0.1 μf |
| 147 | .01 μf |

For physicians who still know how to use it, a stethoscope remains a versatile, effective, and low cost tool for initial diagnosis of a patient and for monitoring a patient's condition during treatment, possibly avoiding the need for expensive diagnostic equipment. An electronic stethoscope constructed in accordance with the invention augments the aural acuity of a physician by giving him full control over processing somatic sounds to facilitate diagnosis.

What is claimed is:

1. An electronic stethoscope comprising:

a microphone;

an active filter coupled to said microphone, said active filter having a center frequency continuously variable within the range of 1 hz to 1500 hz and a bandwidth continuously variable between 1 hz and 3000 hz, wherein said center frequency and said bandwidth are varied indedendently of each other;

an amplifier coupled to said active filter; and an inverse filter coupled to said amplifier, said inverse filter having a frequency response which is the inverse of the frequency response of the human ear.

2. The electronic stethoscope as set forth in claim 1 wherein said active filter includes:

an input terminal and an output terminal;

a first amplifier having an input and an output, wherein the output of said first amplifier is coupled to said output terminal;

a second amplifier having an input and an output;

a first resistor coupling the output of said first amplifier to the input of said second amplifier;

a first potentiometer coupling the output of the second amplifier to the input of the first amplifier, said first potentiometer controlling the center frequency of said active filter;

a second potentiometer coupling said input terminal to the input of said first amplifier, said second potentiometer controlling the bandwidth of said active filter;

a capacitor and a second resistor connected in series and coupled between the input of said first amplifier and electrical ground, whereby said active filter has less than unity gain at all settings of center frequency and bandwidth.

3. The electronic stethoscope as set forth in claim 2 wherein said first potentiometer and said second potentiometer are each a linear potentiometer.

4. The electronic stethoscope as set forth in claim 2 wherein said first potentiometer and said second potentiometer are each a rotary potentiometer.

5. The electronic stethoscope as set forth in claim 1 wherein said active filter includes:

an input terminal and an output terminal;

a first amplifier having an input and an output;

a second amplifier having an input and an output, wherein the output of said second amplifier is coupled to said output terminal;

a third amplifier having an input and an output;

a fourth amplifier having an input and an output;

a first potentiometer coupling said input terminal to the input of said first amplifier;

a second potentiometer coupling the output of the first amplifier to the input of the second amplifier;

a third potentiometer coupling the output of the second amplifier to the input of the third amplifier;

a fourth potentiometer coupling the output of the second amplifier to the input of the fourth amplifier;

wherein said first and fourth potentiometers control bandwidth and said second and third potentiometers control center frequency of said active filter;

a first resistor coupling the output of said first amplifier to the input of said first amplifier;

a second resistor coupling the output of said fourth amplifier to the input of said first amplifier;

a third resistor coupling the output of said third amplifier to the input of said first amplifier;

wherein the resistances of said first resistor to said second resistor to said third resistor are in the approximate ratio of 1:10:100.

6. The electronic stethoscope as set forth in claim 5 and further including:

a fourth resistor coupling the output of said fourth amplifier to the input of said fourth amplifier;

wherein the resistances of said fourth resistor to said second resistor are in the approximate ratio of 1:1.

7. The electronic stethoscope as set forth in claim 1 and further comprising:

a preamplifier coupling said microphone to said active filter, said preamplifier including an input coupled to said microphone, a first output coupled to said active filter, a second output coupled to said amplifier, and a switch for selecting either said first output or said second output, whereby said stethoscope can filter the sounds picked up by said microphone or pass the sounds from said microphone unfiltered to said amplifier.

8. A state variable filter having a bandwidth of at least ten octaves, unity gain or less, and continuously and independently adjustable bandwidth and center frequency, said filter comprising:

an input terminal and an output terminal;

a first amplifier having an input and an output;

a second amplifier having an input and an output, wherein the output of said second amplifier is coupled to said outout terminal;

a third amplifier having an input and an output;

a fourth amplifier having an input and an output;

a first variable resistance coupling said input terminal to the input of said first amplifier;

a second variable resistance coupling the output of the first amplifier to the input of the second amplifier;

a third variable resistance coupling the output of the second amplifier to the input of the third amplifier;

a fourth variable resistance coupling the output of the second amplifier to the input of the fourth amplifier;

wherein said first and fourth variable resistances control the bandwidth and said second and third variable resistances control the center frequency of said filter;

a first resistance coupling the output of said first amplifier to the input of said first amplifier;

a second resistance coupling the output of said fourth amplifier to the input of said first amplifier;

a third resistance coupling the output of said third amplifier to the input of said first amplifier;

wherein the resistances of said first resistance to said second resistance to said third resistance are in the approximate ratio of 1:10:100.

9. The filter as set forth in claim 8 wherein said variable resistances each include a fixed resistor in series with a potentiometer.

10. The filter as set forth in claim 8 and further including:

a fourth resistance coupling the output of said fourth amplifier to the input of said fourth amplifier;

wherein the resistances of said fourth resistance to said second resistance are in the approximate ratio of 1:1.

11. A Butterworth filter having a bandwidth of at least ten octaves and continuously and independently adjustable bandwidth and center frequency, said filter comprising:

an input terminal and an output terminal;

a first amplifier having an input and an output, wherein the output of said first amplifier is coupled to said output terminal;

a second amplifier having an input and an output;

a first resistor coupling the output of said first amplifier to the input of said second amplifier;

a first potentiometer coupling the output of the second amplifier to the input of the first amplifier, said first potentiometer controlling the center frequency of said filter;

a second potentiometer coupling said input terminal to the input of said first amplifier, said second potentiometer controlling the bandwidth of said filter;

a capacitor and a second resistor connected in series and coupled between the input of said first amplifier and electrical ground, whereby said active filter has less than unity gain at all settings of center frequency and bandwidth.

12. A hand-held electronic stethoscope comprising:

a case having a front and a back interconnected by a first side, a second side, a top, and a bottom, said case fitting within a hand;

an hole in said top;

a resilient collar in said hole;

a microphone fitting within said resilient collar and insulated from vibrations in said case by said collar;

electronic circuitry within said case and coupled to said microphone for amplifying sounds received by said microphone;

three controls coupled to said circuitry, said controls located in either said first side or said second side;

whereby said stethoscope can be held in one hand and said controls adjusted by said hand.

13. The electronic stethoscope as set forth in claim 12 wherein said circuitry includes an active filter and wherein two of said three controls separately and continuously vary the center frequency and bandwidth of said active filter.

14. The electronic stethoscope as set forth in claim 13 wherein said three controls are rotary controls located in said first side.

15. The electronic stethoscope as set forth in claim 13 wherein said two of said three controls are linearly actuated and are located in said front of said case, and wherein said two controls independently vary the center frequency and the bandwidth of said active filter.

16. The electronic stethoscope as set forth in claim 15 wherein the third of said controls is located in said first narrow side.

17. The electronic stethoscope as set forth in claim 12 and further including at least one LED in said top for indicating the operation of said circuitry.

* * * * *